US00PP29514P3

(12) United States Plant Patent
Sorensen

(10) Patent No.: US PP29,514 P3
(45) Date of Patent: Jul. 17, 2018

(54) ***ANEMONE* PLANT NAMED '2015 7 NFB'**

(50) Latin Name: *Anemone japonica*
Varietal Denomination: 2015 7 NFB

(71) Applicant: Lily Sorensen, Vester Skerninge (DK)

(72) Inventor: Lily Sorensen, Vester Skerninge (DK)

( * ) Notice: Subject to any disclaimer, the term of this patent is extended or adjusted under 35 U.S.C. 154(b) by 85 days.

(21) Appl. No.: 15/330,501

(22) Filed: Sep. 28, 2016

(65) Prior Publication Data

US 2018/0092269 P1 Mar. 29, 2018

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Cassandra Bright

(57) ABSTRACT

A distinct new cultivar of *Anemone* plant named '2015 7 NFB', characterized by fully double flowers which are white, with an occasional light pink blush. The new cultivar is an *Anemone* typically suited for ornamental container and landscape use.

2 Drawing Sheets

Latin name of the genus and species: *Anemone japonica*.
Variety denomination: '2015 7 NFB'.

BACKGROUND OF THE INVENTION

The new *Anemone* was discovered by the inventors, Lily Sorensen as a product of chance discovery. The new variety was discovered as a naturally occurring, whole plant mutation of the unpatented variety *Anemone japonica* 'Honorine Jobert' at a commercial nursery in Denmark.

Asexual reproduction by tissue culture was first undertaken in the Fall of 2014, by at a commercial laboratory in The Netherlands. Plants produced subsequently have proved to be stable and reproduced true to type in successive generations.

SUMMARY OF THE INVENTION

The cultivar '2015 7 NFB' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of '2015 7 NFB'. These characteristics in combination distinguish '2015 7 NFB' as a new and distinct *Anemone* cultivar:

1. True double flowers.
2. White flowers, with an occasional light pink blush.

PARENTAL COMPARISON

Plants of the new cultivar '2015 7 NFB' are similar to the parent in most horticultural characteristics. However, plants of '2015 7 NFB' differ in that they produce truly double flowers, whereas the seed parent produces single, pure white flowers. Additionally flowers of the parent variety are pure white, flowers of the new variety can have an occasional light pink blush coloration.

COMMERCIAL COMPARISON

Plants of the new cultivar '2015 7 NFB' are similar to the known commercial variety, *Anemone hybrida* 'Macane001', U.S. Plant Pat. No. 23,132, in some horticultural characteristics. However, plants of '2015 7 NFB' differ in the following:

1. '2015 7 NFB' has a fully double flower, this comparator has a single flower.
2. Flowers of the new variety are white; or white with a pink blush. Flower color of this comparator are white with violet-blue flushing.

Plants of the new cultivar '2015 7 NFB' are similar to the known commercial variety, *Anemone* 'Pretty Lady Emily' U.S. Plant Pat. No. 22,303 in some horticultural characteristics. However, the new variety produces white flowers, or white with an occasional light pink blush which are fully double, compared to the pink, semi-double flowers of this comparator.

BRIEF DESCRIPTION OF THE PHOTOGRAPHS

Figure 1:
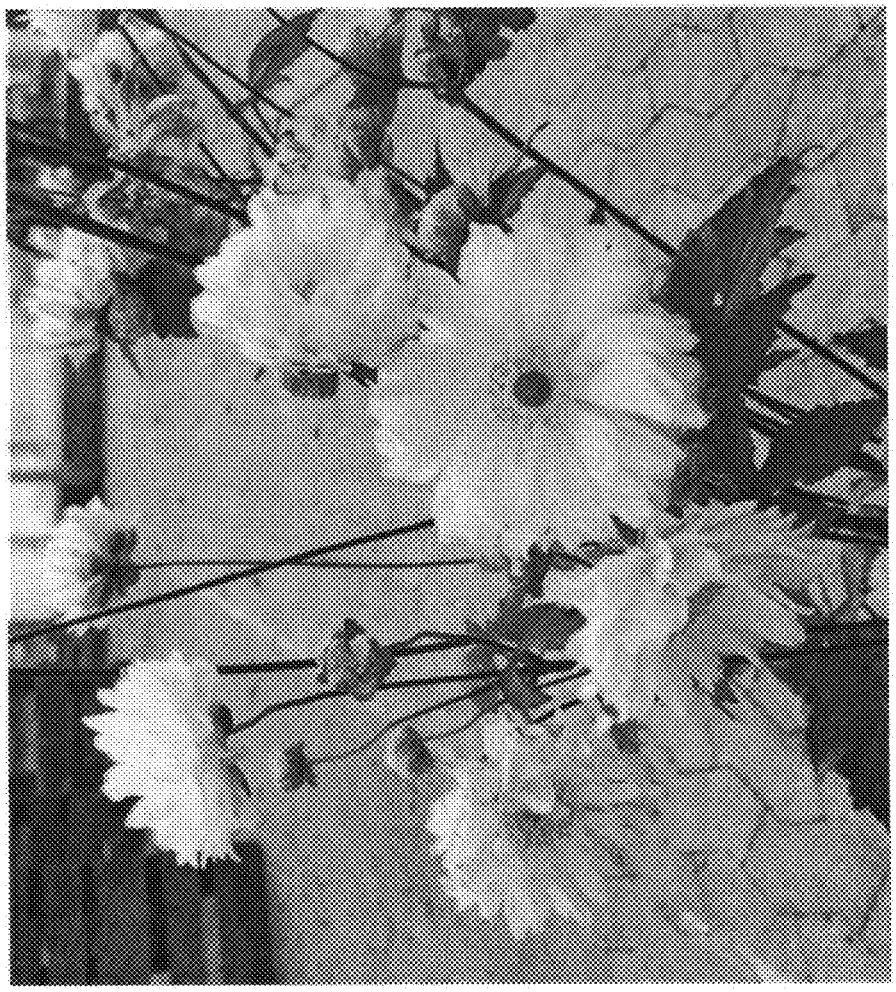

The accompanying photograph in FIG. 1 illustrates in full color typical flowers of '2015 7 NFB' grown outdoors in in Denmark. This plant is approximately 12 months old.

Figure 2:
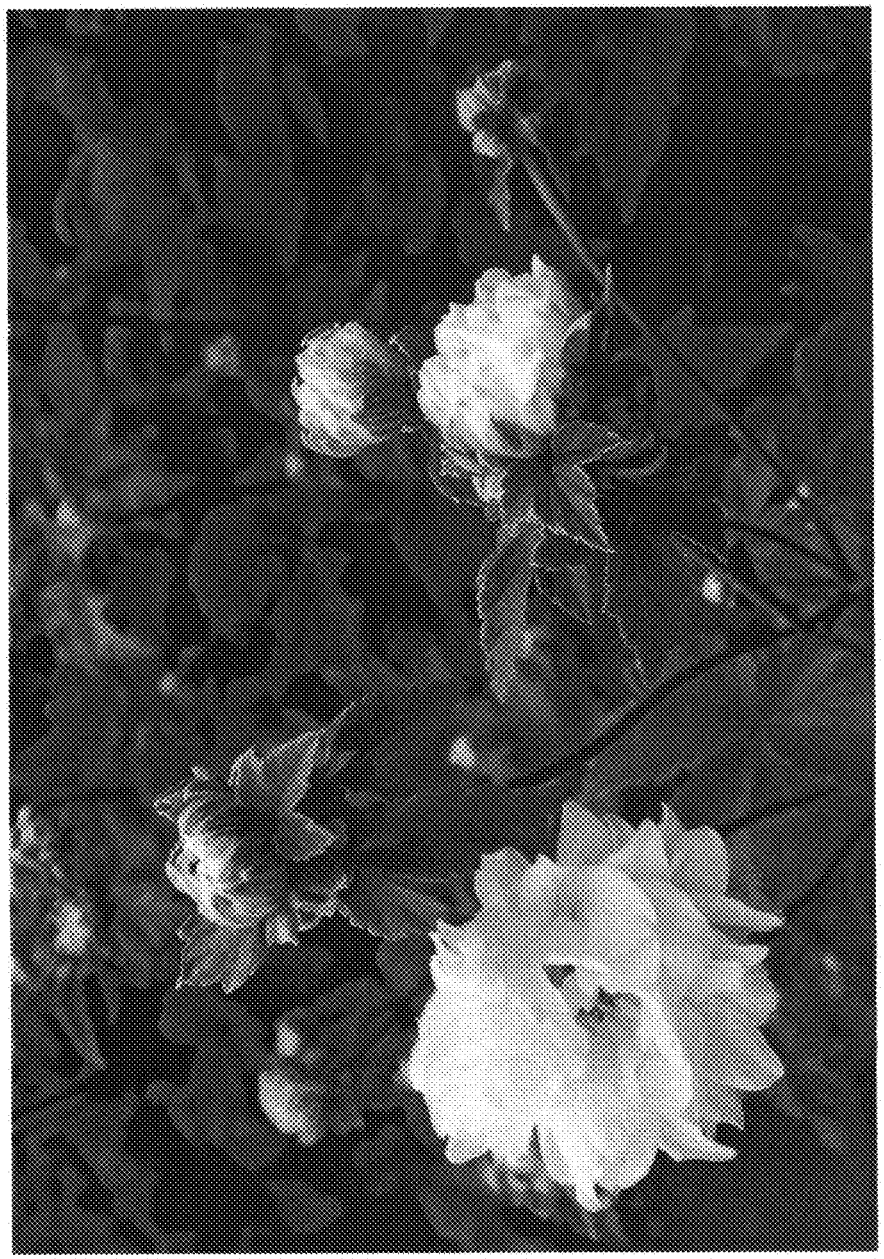

FIG. 2 illustrates a close up of the flower and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe '2015 7 NFB' plants grown outdoors in Denmark, at a commercial nursery. The growing temperature ranged from approximately 5° C. to 18° C. during the day, and night temperatures ranging from approximately −5° C. to 12° C. No artificial light, photoperiodic treatments or chemical treatments were given to the plants. Measurements and numerical values represent averages of typical flowering types.

Botanical classification: *Anemone japonica* '2015 7 NFB'.

Age of the plant described: Approximately 12 months.

Container size of the plant described: 2 liter commercial container.

PROPAGATION

Time to produce a flowering plant from root-cutting: About nine to twelve months.

Root description: Fibrous, grey-brown, not accurately measured with an R.H.S. chart.

Rooting habit: Dense, freely branching.

PLANT

Growth habit: Upright.

Pot size of plant described: 2 liter circular pot (14 cm).

Height: 39 cm it top of foliage plane. 65 to 70 cm to top of flowering plane.

Plant spread: 30 cm.

Growth rate: Moderate.

Branching characteristics: No lateral branches, flowering stems grow from a basal Rosette.

FOLIAGE:

Leaf:

*Arrangement*.—Basal rosette.

*Shape*.—Overall deltate, tri-lobed.

*Quantity*.—Average 40 per plant.

*Average length*.—8 to 14 cm.

*Average width*.—8 to 13 cm.

*Apex*.—Acute.

*Base*.—Cordate.

*Margin*.—Biserrate.

*Texture of up error and lower surface*.—Matte.

*Pubescence*.—Upper side covered with very short adpressed hairs, lower side glabrous.

*Aspect*.—Somewhat cupped and upwardly facing.

*Color*.—Young foliage upper side: Near RHS Green 137A. Young foliage under side: Near RHS Green 138B. Mature foliage upper side: Near RHS Green 137C. Mature foliage under side: Near Green 138C.

*Venation*.—Type: Pinnate. Venation color upper side: Near RHS Yellow-Green 144C. Venation color under side: Near RHS Yellow-Green 144D.

*Petiole*.—Length: 12 to 20 cm. Diameter 2 to 4 mm. Color: Near RHS Yellow-Green 144B, occasionally slightly tinged Greyed-Red 178A. Texture: Densely covered with short hairs.

*Stipule description*.—Length: 1.8 cm. Diameter: 0.9 cm. Color: Near RHS 145B; flushed N186C. Texture: Densely covered with short hairs, average length: 0.1 cm, colored near RHS N155D.

FLOWER

Natural flowering season: Midsummer until Fall.

Days to flowering from rooted cutting: 9-12 months.

Inflorescence and flower type and habit: Inflorescence a terminal corymb, individual flowers rotate, double. Flowers sometimes occur 3 at a node, however at different maturity stages.

Rate of flower opening: About 14 days from bud to fully opened flower.

Flower longevity on plant: Approximately two weeks.

Persistent or self-cleaning: Self-cleaning.

Bud:

*Shape*.—Globular.

*Length*.—1.5 cm.

*Diameter*.—2.0 cm.

*Color*.—Near RHS Green 138A and Green-White 157A.

Flower size:

*Diameter*.—5.5 to 6.8 cm.

*Depth*.—3.0 cm.

*Aspect*.—Outward and upright facing.

Tepals:

*Quantity*.—40 to 60.

*Arrangement*.—Rotate, overlapping.

*Length*.—2.7 cm.

*Width*.—0.8 cm.

*Shape*.—Spatulate to ovate.

*Apex*.—Obtuse to broad acute.

*Base*.—Attenuate.

*Margin*.—Entire.

*Texture, upper and lower surfaces*.—Glabrous, matte.

*Color*.—When opening, upper surface: Near RHS White 155B. When opening, lower surface: Near RHS Yellow-Green 145C, irregular lightly tinged 59D. Fully opened, upper surface: Near RHS N155D, occasionally very lightly tinted 65C towards apex. Fully opened, lower surface: Near RHS N155D slightly tinged 65C and 70B towards apex.

Bracts: Broad claw like shape, 1.8 long 1.0 wide. Truncate base, acute apex, or 3 lobed acute apex. Interior color 138B, facing to 138C base an lower margin near white 155A, Apex occasionally blotched 59C. Exterior color same as interior color. Glabrous texture.

Longest peduncles:

*Length*.—32 cm.

*Diameter*.—0.35 cm.

*Angle*.—About 90° to basal rosette, straight or very slight undulation.

*Strength*.—Moderately strong.

*Texture*.—Densely covered with very short soft hairs.

*Color*.—Near RHS Yellow-Green 147C, tinged Greyed-Purple 186B.

Shortest peduncles:

*Length*.—10 cm.

*Diameter*.—0.3 cm.

*Angle*.—About 15° to the peduncle.

*Strength*.—Moderately strong.

*Texture*.—Slightly glossy, densely covered with short soft hairs, average length: 0.075 cm, colored near RHS N155D.

*Color*.—Near RHS Yellow-Green 147C, tinged Greyed-Purple 186B.

Fragrance: Faint musty scent.

REPRODUCTIVE ORGANS

Stamens:

*Number*.—Average: 120.

Anthers:

*Shape*.—Oblong.

*Length*.—Approximately 0.15 cm.

*Color*.—Near RHS Yellow-Orange 17A.

*Pollen*.—Color: Near RHS Yellow-Orange 21A. Quantity: scant.

Pistil:

*Number*.—Average: 180.

*Length*.—0.2 cm.

*Style*.—Length: 0.15 cm. Color: Near RHS White 155C.

*Stigma*.—Shape: Linear. Color: Near RHS Yellow-Green 144C. Ovary Color: Near RHS White 155C.

OTHER CHARACTERISTICS

Seed/fruit: No seeds/fruits detected to date.

Temperature tolerance: Plants of the new *Anemone* h are hardy to at least USDA Zone 6.

Diseases and pests: Neither resistance nor susceptibility to normal diseases and pests of *Anemone* has been observed.

What is claimed is:

1. A new and distinct cultivar of *Anemone japonica* plant named '2015 7 NFB' as herein illustrated and described.

* * * * *